(12) United States Patent
Offord Cavin et al.

(10) Patent No.: US 7,202,082 B2
(45) Date of Patent: Apr. 10, 2007

(54) IMMORTALIZED PREOSTEOBLASTS AND METHOD FOR THEIR PRODUCTION

(75) Inventors: Elizabeth Offord Cavin, Poliez-Pittet (CH); Christian Darimont-Nicolau, Lausanne (CH); Catherine Mace, Lutry (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 10/422,996

(22) Filed: Apr. 25, 2003

(65) Prior Publication Data

US 2003/0186438 A1    Oct. 2, 2003

Related U.S. Application Data

(63) Continuation of application No. PCT/EP01/12441, filed on Oct. 26, 2001.

(30) Foreign Application Priority Data

Oct. 27, 2000    (EP) .................. 00123570

(51) Int. Cl.
*C12N 5/08*      (2006.01)
*C12N 15/63*     (2006.01)
*C12Q 1/00*      (2006.01)
*A61K 48/00*     (2006.01)

(52) U.S. Cl. .................. 435/366; 435/455; 435/4

(58) Field of Classification Search ................ 435/455, 435/456, 325, 366, 372, 375, 377; 536/23.1, 536/23.72
See application file for complete search history.

(56) References Cited

U.S. PATENT DOCUMENTS 6,399,384 B1 *  6/2002  Jat .................. 435/456

FOREIGN PATENT DOCUMENTS

| WO | WO/93 23572 A | 11/1993 |
| WO | WO/95 02687 A | 1/1995 |
| WO | WO/95 13383 A | 5/1995 |
| WO | WO/99 39724 A | 8/1999 |
| WO | WO/01 21790 A | 3/2001 |

* cited by examiner

*Primary Examiner*—Quang Nguyen
(74) *Attorney, Agent, or Firm*—Winston & Strawn LLP

(57) ABSTRACT

The present invention relates to novel immortalized pre-osteoblast cell lines derived from the periost and capable of differentiate to osteoblasts. In particular, the present invention pertains to the use of such cell lines in assays for detecting substances controlling the differentiation of pre-osteoblasts to osteoblasts and for detecting substances enabling improved bone formation, maintenance of bone mass, bone repair and for preventing the onset of osteoporosis.

3 Claims, 6 Drawing Sheets

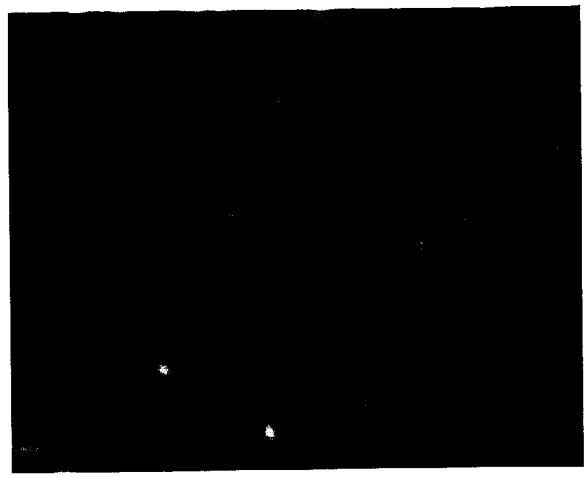
Figure 1. Immunofluorescent staining of hPOB cells with anti-SV40 T-antigen antibody

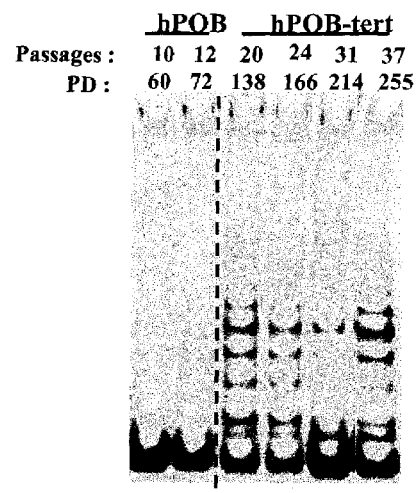
Figure 2. Telomerase activity in precisis and hTERT expressing human bone cells
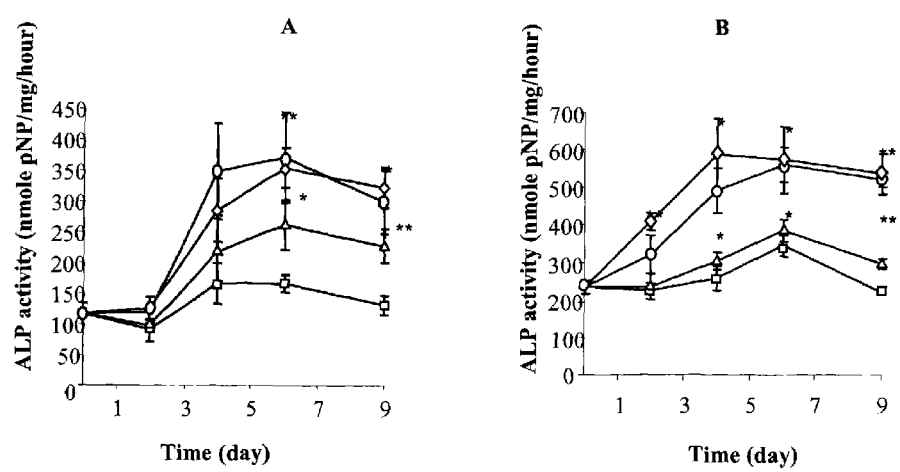
Figure 3. Alkaline phosphatase activity in hPOB (A) and hPOB-tert (B) cells during differentiation

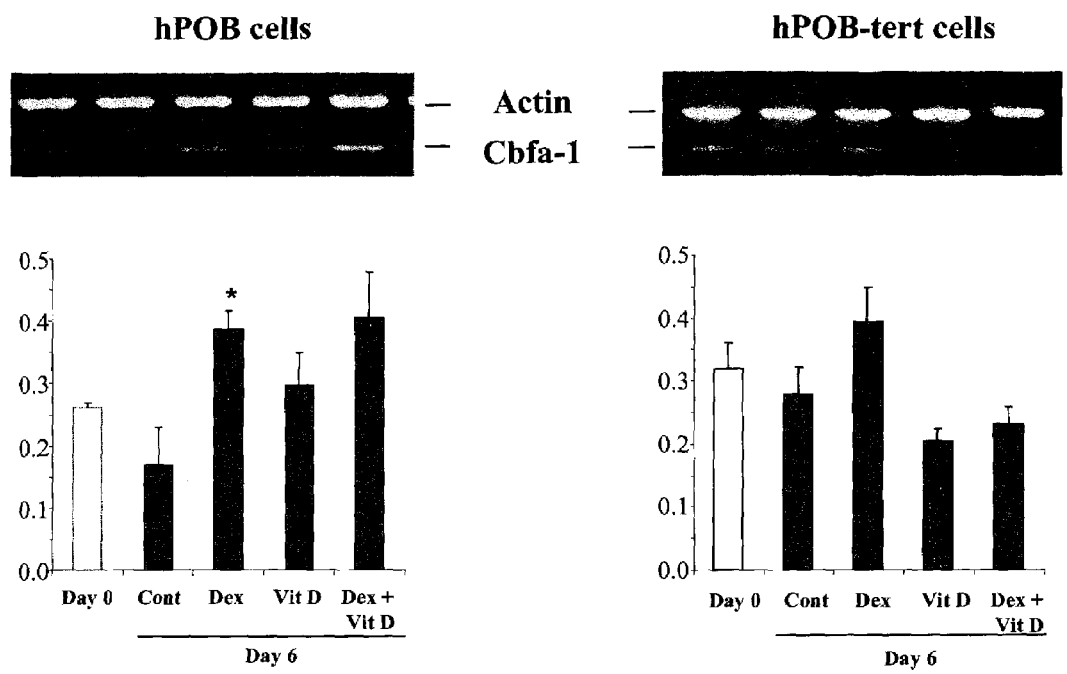
Figure 4. Expression of bone-specific transcription factor Cbfa-1 in confluent and differentiated hPOB and hPOB-tert cells

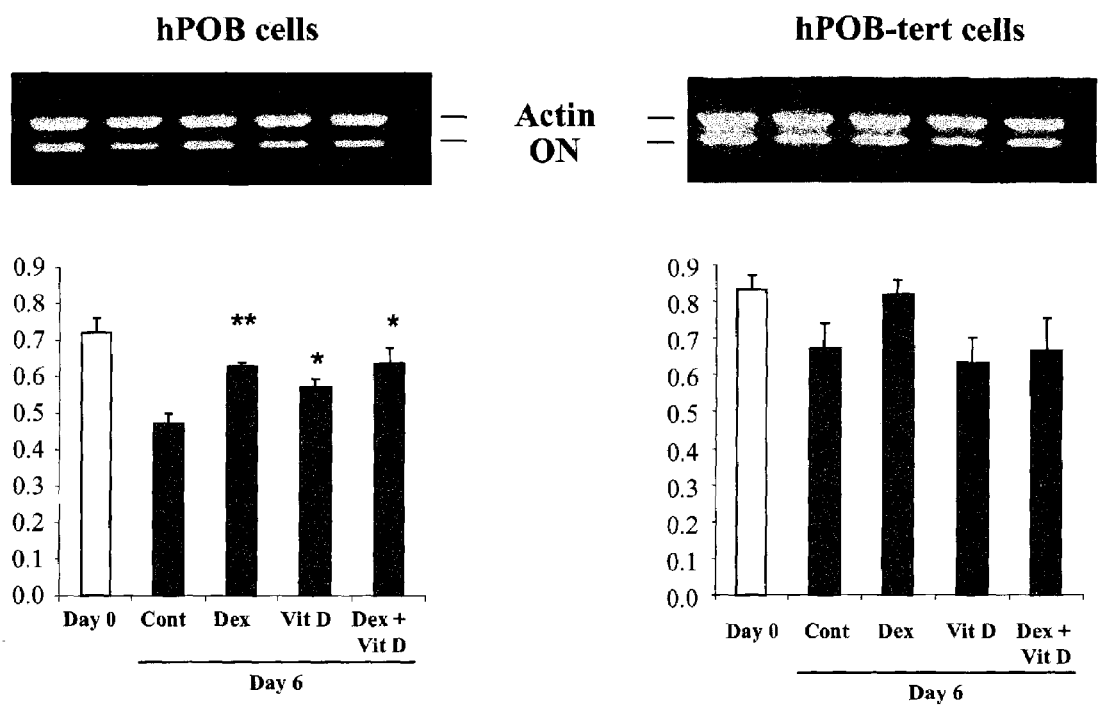
Figure 5. Expression of osteonectin in confluent and differentiated hPOB and hPOB-tert cells

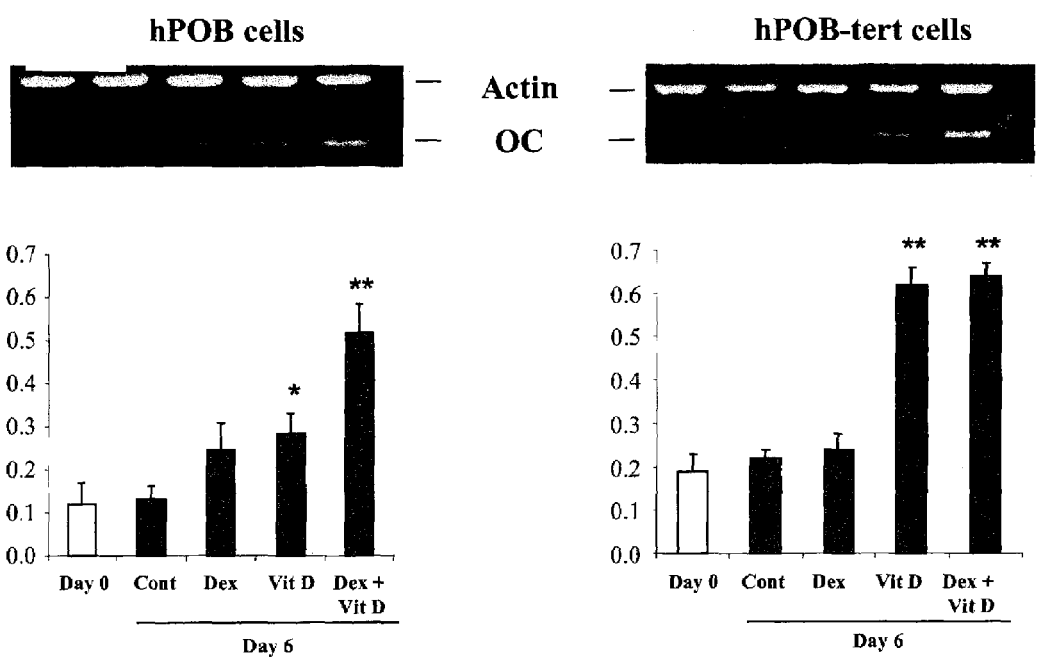
Figure 6. Expression of osteocalcin in confluent and differentiated hPOB and hPOB-tert cells A  B
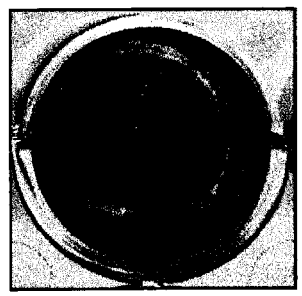 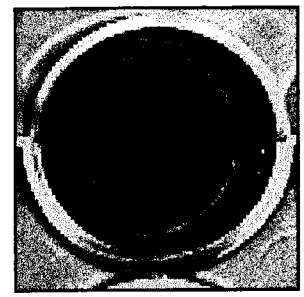
Figure 7. Mineralization of the extracellular matrix by hPOB and hPOB-tert cells

IMMORTALIZED PREOSTEOBLASTS AND METHOD FOR THEIR PRODUCTION

CROSS-REFERENCE TO RELATED APPLICATIONS

This application is a continuation of the US national phase of International application PCT/EP01/12441 filed Oct. 26, 2001, the content of which is expressly incorporated herein by reference thereto.

BACKGROUND ART

The present invention relates to novel immortalized preosteoblast cell lines derived from the periosteal layer of bones which are capable of differentiating to osteoblasts. In particular, the present invention pertains to the use of such cell lines in assays for detecting substances controlling the differentiation of periosteally derived-preosteoblasts to osteoblasts and for detecting substances enabling improved bone formation, maintenance of bone mass, bone repair and for preventing the onset of osteoporosis.

In bone tissues, bones are constantly destructed, resorbed and created de novo by recurrent processes controlled on the cellular level by osteoblasts and osetoclasts, respectively. Osteoblasts are primarily involved in the process of bone formation, while the process of bone destruction and resorption of the bone material seems to be mediated by osteoclasts.

Bones are constituted of two major zones, an inner zone called "substantia spongosia", and an outer zone, which is called "substantia corticalis". Said outer zone harbors the Havers channels and the periost. The periost, the so called skin of the bones, covers the circumference of all bones with the proviso of those employed in joints. The periost primarily provides the bones with vessels, ascertains the attachment of tendons and harbors a plurality of nerves. Recently, it has been found that the periost also seems to participate in bone growth and furthermore in (bone) regenerating processes of an individual, such as bone repair after fracture.

The periost itself is composed of two major areas, the outer part, termed "stratum fibrosum", which mainly contains connecting tissue, and the "Kambium" or "stratum osteogenicum", which is adjacent to the bone itself and comprises a number of non-differentiated cells, such as e.g. preosteoblasts. It is presently hypothesized that these preosteoblasts, or the cells derived therefrom, seem to participate in bone fracture repair and/or other reconstitutive processes. These preosteoblasts are, however, seemingly different from preosteoblasts found in the "substantia spongosia", since said cells are deemed to lack the capability of differentiating into adipocytes and are supposed not to support osteoclast differentiation.

During ageing an individual is subject to a gradual loss in bone mass involving a widening of the Havers channels in the substantia corticalis and a reduction in mass of the substantia spongosia. This phenomenon is mainly due, on the cellular level, by bone resorption of osteoclasts exceeding bone formation by osteoblasts, which condition is termed uncoupling. In case the uncoupling persists for a longer period of time, more and more of the bone's material gets destructed/resorbed finally generating a disease termed osteoporosis. Osteoporosis causes pain in the bone and renders the bone fragile, eventually leading to fracture thereof and lumbago.

In the past osteoporosis has been treated by various regimens, involving increasing the calcium intake, light exercises, sun tan or administering compounds increasing the activity of osteoblasts present in the "substantia spongosia". In this respect, the U.S. Pat. No. 5,002,968 discloses an organogermanium compound for activating proliferation of osteoblasts so as to stimulate bone formation and to balance the surpassing activity of osteoclasts. Further, in EP 0 725 080 a novel protein, the basic osteoblast growth factor II (bOGF-II) is disclosed, which is capable to stimulate osteoblast growth.

However, quite recently it was found that osteoblasts not only perform a task in ossification but also seem to play a role as a control center for the bone reformation phenomenon that is closely related to the differentiation and activation of osteoclasts, the cells mediating bone degradation. In view of this, the mere activation of existing osteoblasts for the promotion and maintenance of bone mass is now rather doubted to be efficient.

Concurrently, it has been found that at the same time as bone loss is occurring within the bones, bone is being added to the periostal surface, yet more slowly than during growth, indicating this process is contravening the destabilization of bones effected by bone degradation.

It would therefore be interesting to evaluate and study the osteoblasts present in the periost and their action on bone repair and bone build up so as to provide substances that influence said processes in the periost. In order to provide such compounds, effective means for elucidating the effect thereof on cells involved in bone metabolism are in need.

As is acknowledged in the art the best means for performing such experiments are cells involved in said processes. However, cells directly obtained from a donor, the so called primary cells, have a limited proliferative lifespan only, which restricts the use thereof for in vitro studies. In addition, not all type of cells may be isolated and cultured. This applies in particular to precursor cells that often may not be isolated in sufficient quantity so that experiments on said cells may be carried out.

In the past, though some cells proved to be resistant to a manipulation of this kind, the proliferation of certain cells, as e.g. intestinal or corneal cells, could be extended by infecting cells of a primary cell culture with oncogenes, such as the siminian virus 40 large T antigen (SV40 T antigen). The SV40 large T-antigen is known to effect inactivation of proteins playing a key role in cell cycle progressing, in particular the p53 and the retinoblastoma (pRb) protein. However, though the (over-)expression of such oncogenes in human primary cells could extend the proliferation of said cells for a limited number of cell divisions, said cells eventually stop growing at a stage called "crisis". During this stage, which normally occurs at about passage 10 to 20 the cells remain viable in a state named "senescence" or simply die. In rare cases, some cells may escape from this state and start to proliferate again. This capability to start proliferation de novo is accounted for by genomic reorganisation through additional epigenic events taking place in the cell. Yet, these substantial genome modifications most often result in the cells loosing the initial characteristic of the primary cells they are derived from.

Consequently, a problem underlying the present invention is to provide a means for further determining substances influencing bone formation and various effects thereof on bone metabolism.

SUMMARY OF THE INVENTION

The present invention solved the above problem by providing novel immortalized preosteoblast cell lines derived from the periostal layer of bones capable of differentiating to osteoblasts.

The cell lines of the present invention are capable of being cultured for at least 60, more preferably at least 80 and even more preferred at least 100 passages in culture. In addition, it has been surprisingly shown that the phenotype of cells of the primary culture has been essentially maintained.

The present cell lines may be obtained according to a method that comprises the steps of (a) isolating preosteoblasts from a suitable source, (b) transfecting the cells with a construct carrying a gene uncoupling the normal cell cycle, (c) optionally isolating transfected cells from the culture, (d) transfecting cells obtained in step (b) or (c) with a construct allowing the expression of the telomerase reverse transcriptase gene; and (e) selecting the cells of step (d) to obtain cells containing both genes incorporated therein.

The present invention further pertains to methods for detecting substances controlling the differentiation of pre-osteoblasts to osteoblasts and for detecting substances enabling improved bone formation, maintenance of bone mass, bone repair and for preventing the onset of osteoporos, which comprises preparing the cell lines of the present invention and using the cell line in an assay for detecting substances controlling the differentiation of pre-osteoblasts to osteoblasts and for detecting substances enabling improved bone formation, maintenance of bone mass, bone repair and for preventing the onset of osteoporos.

IN THE FIGURES

FIG. 1 shows immunostaining of hPOB cells with a monoclonal antibody directed against the human SV40 T antigen; confluent cells were stained by an immunofluorescent method using a primary antibody specific to human SV40 T antigen;

FIG. 2 shows the telomerase activity in hPOB and hPOB-tert cells; lane 1: telomerase activity in control condition, i.e. without cells; lane 2 and 3: telomerase activity in hPOB cells at two different passages; lane 4 to 10: telomerase activity in hPOB-tert cells at different passages.

FIG. 3 shows the regulation of alkaline phospatase activity during the differentiation of hPOB and hPOB tert cells; alkaline phosphatase activity was measured before confluence (day—1) and at days 2, 4, 6 and 9 after confuence in hPOB cells (A) and hPOB-tert cells (B), incubated with no effectors (○) 10 nM dexamethasone (△), 10 nM Vitamine D (●) or with both effectors (■). Data are the means±SEM of at least three experiments. Values statistically different from untreated cells are indicated by * ($p<0.05$); ** ($p<0.01$).

FIG. 4 shows the regulation of Cbfa-1 expression in hPOB and hPOB tert cells; RNA from hPOB (A) and hPOB-tert cells (B) cultured for 6 days without effectors or in the presence of 10 nM dexamethasone, 10 nM Vitamine D or with both effectors, were prepared. Cbfa-1 and actin RNA expression was analysed in parallel by semi-quantiative RT-PCR. Signals obtained were quantified and actin was taken as internal standard. Data are the means±SEM of at least three experiments. Values statistically different from untreated cells are indicated by * ($p<0.05$).

FIG. 5 shows the regulation of osteonectin expression in hPOB and hPOB tert cells; RNA from hPOB (A) and hPOB-tert cells (B) were cultured for 6 days without effectors or in the presence of 10 nM dexamethasone, 10 nM Vitamine D or with both effectors, were prepared; Osteonectin and actin RNA expression was analysed in parallel by semi-quantiative RT-PCR; signals obtained were quantified and actin was taken as internal standard; data are the means±SEM of at least three experiments; values statistically different from untreated cells are indicated by * ($p<0.05$); ** ($p<0.01$).

FIG. 6 shows the regulation of osteocalcin expression in hPOB and hPOB tert cells; RNA from hPOB (A) and hPOB-tert cells (B) cultured for 6 days without effectors or in the presence of 10 nM dexamethasone, 10 nM Vitamine D or with both effectors, were prepared; osteocalcin and actin RNA expression was analysed in parallel by semi-quantiative RT-PCR; signals obtained were quantified and actin was taken as internal standard; the data are the means±SEM of at least three experiments. Values statistically different from untreated cells are indicated by * ($p<0.05$); ** ($p<0.01$).

FIG. 7 shows the mineralization of the extracellular matrix by hPOB and hPOB-tert cells; hPOB (A) and hPOB-tert (B) cells were cultured in the presence of 10 nM dexamethasone and 10 nM Vitamin D; at day 21, cells were fixed and stained by the Alzarin-red as described in Material and Methods.

DETAILED DESCRIPTION OF PREFERRED EMBODIMENT

In the experiments leading to the present invention the inventors transfected primary osteoblast precursor cells obtained from the periosteal bone of healthy human adults with a construct containing DNA sequences encoding the SV40 large T antigen. The cells thus obtained (called hPOB cells) were able to differentiate into osteoblast like cells exhibiting a phenotype essentially identical to that of primary osteoblasts, as determined by alkaline phosphatase activity, the expression of specific markers such as the Osteoblast Specific Factor-1 (OSF-1 or Cbfa-1), osteopontin and osteocalcin, and the capacity to form mineralized nodules. However, those cells were expected to have only a limited extended life span and then to enter into crisis with a cell cycle arrest at the G1 phase.

These cells were then transfected with a construct bearing the telomerase reverse transcriptase gene (Bodnar, A. G., et al., *Extension of life-span by introduction of telomerase into normal human cells*. Science, 1998. 279(5349): p. 349–52). Upon further passaging the transfected cells called hPOB-tert, it was discovered that those cells did not enter crisis but continued to proliferate. Therefore, transfecting pre-immortalized cells with a construct carrying the telomerase gene allows to obtain truly immortalized cell line, wherein no genome reorganization took place. This is so because the cells did not essentially change their genomic structure, and the gene transcription and expression is essentially identical to that of the cells of the primary culture.

The cell lines of the present invention are capable of being cultured for at least 60, more preferably at least 80 and even more preferred at least 100 passages in culture. In detail, the cell lines according to the present invention are really immortal and may be cultured in vitro as long as desired. They may be prepared from any source, from which preosteoblasts derived from the periostal layer of bones may be obtained, in particular from mammals, such as humans. According to a preferred embodiment the cell line is one that has been deposited with the Institute Pasteur according to the Budapest Treaty on Oct. 25th, 2000 and that received the accession no. CNCM I-2573.

In addition, it has been surprisingly shown that the phenotype of cells of the primary culture has been essentially maintained. In particular, the periosteally derived cells of the present invention are capable of differentiating to osteoblasts, the cell responsible for bone mass formation in this area. This feature is of particular interest for studying the development of bone formation and bone repair.

The preosteoblast cell lines of the present invention also exhibit an essentially identical phenotype as compared to the cells of the primary cell culture, from which they are derived. In particular, they show an alkaline phosphatase activity, expression of specific markers such as Osteoblast Specific Factor-1 (OSF-1 or Cbfa-1), osteopontin and osteocalcin etc, and a capacity to form mineralized nodules which is essentially the same as found in the cells of the primary culture.

In case of differentiating the preosteoblast cell lines to osteoblasts according to the present invention by stimulating the cells with agents inducing such a differentiation, such as e.g. by stimulating them with a mixture of dexamethasone and vitamin D3, the osteoblasts obtained also exhibit essentially the same differentiation markers as an osteoblast cell obtained directly from a donor. In this respect it has been shown that the level of alkaline phosphatase, specific markers such as Osteoblast Specific Factor-1 (OSF-1 or Cbfa-1), osteopontin and osteocalcin, and the capacity to form mineralized nodules of osteoblasts derived from the present cell lines by inducing differentiation are essentially the same as compared to osteoblasts found the being from which they are derived.

In summary, the cell lines of the present invention exhibit an essentially identical morphological pattern as compared to cells of a primary culture they are derived from, and may differentiate into osteoblasts. Therefore, it may be concluded that due to the combined means of pre-immortalization and expression of telomerase the genomic organization of the cells is maintained.

The present cell lines may be obtained according to a method that comprises the steps of (a) isolating preosteoblasts from a suitable source, (b) transfecting the cells with a construct carrying a gene uncoupling the normal cell cycle, (c) optionally isolating transfected cells from the culture, (d) transfecting cells obtained in step (b) or (c) with a construct allowing the expression of the telomerase reverse transcriptase gene; and (e) selecting the cells of step (d) to obtain cells containing both genes incorporated therein.

In a first step (step (a)) preosteblast cells are isolated from the periost of an individual. These cells are transferred into culture, and are subsequently transfected with a construct carrying one or more genes capable of uncoupling the normal cell cycle, such as e.g. genes, the products thereof bind and inactive the protein products of the p53 and the retinoblastoma genes, thus allowing the pimary cells to extend their lifespan. This may be achieved by stably transfecting cells with a recombinant vector, such as with a recombinant plasmid, or a linear piece of DNA having at its ends DNA sequences homologous to endogenous DNA sequences of the cellular genome. This technique allows for an integration of the linear DNA containing the construct into the host's chromosome with the concurrent advantage of its transmittal to progenitor cells. Alternatively the cells may also be infected with a recombinant virus, e.g. a virus carrying the large T antigen gene of the SV40 virus (Simian Virus) or the E6/E7 genes of HPV virus (Human Papilloma Virus).

The cells thus treated may then be selected for cells harboring the construct introduced, which may be effected by simply culturing the cells for a few additional passages. Cells, in which the construct has been introduced, will exhibit an extended lifespan and continue to proliferate in culture, while non transfected cells will stop growing. Alternatively a selection marker may be included in the construct and transfected cells may be selected for the presence of the marker.

The cells thus selected are then transfected with a construct, with which the telomerase gene contained therein may be expressed. This may be achieved by the same methods as described before, i.e. using a recombinant vector, a linear piece of DNA relying on the phenomenon of homologous recombination or by infecting the cells with a recombinant retrovirus, each carrying the telomerase gene. Apart from the gene encoding the telomerase gene the construct will contain regulatory sequences controlling the transcription of the gene operably linked to the regulatory sequences. As such a regulatory sequence, a promotor sequence controlling the transcription of an adjacent DNA sequence is envisaged.

The cells thus obtained may then be selected for immortalized cells, containing both of the genes introduced in the prior method steps, which may e.g. be effected by diluting the cells and assessing, whether a crisis occurs in the different cultures or not. Moreover, the genomic material of the cells themselves may be assessed for the presence of the different constructs by isolating DNA material from the cells and determining the presence of the genes introduced, which may e.g. be effected by PCR-technology etc.

Consequently, according to a preferred embodiment the present invention pertains to a method for searching for substances useful in influencing the development of preosteoblasts to osteoblasts which comprises preparing the cell lines of the present invention and using the cell lines in an assay for searching for substances useful in influencing the development of preosteoblasts to osteoblasts. According to a more preferred embodiment the present cell lines are used in a method for finding substances directing the differentiation of the preosteoblasts to osteoblasts. This might be of particular interest in case more osteoblasts shall be present in the bone's of an individual for improving bone formation itself or assisting in the maintenance of bone mass and bone repair. In addition, since the preosteoblasts and osteoblasts, respectively, present in the periost seem to participate in bone structural events, such as e.g. during degradation of the inner bone mass with a potential concurrent bone build up in the periphery of the bones, that is in the periost, the cell lines of the present invention are also perfectly suited for searching for substances prolonging or even preventing the onset of osteoporosis by specifically activating bone formation in the periost.

EXAMPLES

The following examples are given for illustrative purposes and are not intended to limit the present invention.

Material and Methods

Material

Cell culture material, media and fetal bovine (FBS) serum were purchased from Gibco BRL (Basel; Switzerland). Alizarin Red S and vitamin $D_3$, $1\alpha,25$-dihydroxy were purchased from Sigma (Buchs; Switzerland) and Calbiochem (Lucerne; Switzerland), respectively. Ascorbic acid and β-glycerophosphate were obtained from Merck (Switzerland).

Example 1

Preparation and Amplification of the Retroviral Vectors

A recombinant retroviral vector carrying the large T antigen gene of Simian Virus (SV40-T antigen) or the human telomerase reverse transcriptase (hTERT; provided by CAMBIA, Canberra, Australia) were constructed by insertion, with standard recombinant DNA techniques, into the BamHI site of the pLHXSD retroviral vector (Stockschlaeder et al., Hum Gene Ther. 2 (1991), 33–39) containing the histidinol gene as selection marker.

Infectious recombinant virus particles were generated through transfection of the recombinant retroviral vector into the amphotropic packaging cell line Phoenix (Clontech), followed by co-culturing with the ecotropic packaging cell line, Psi2, available in the ATCC, to allow "ping-pong" infection to produce a high-titer virus (Lynch C, Miller D. 1991). Production of high helper virus-free retroviral vectors was performed by cocultivation of packaging cells harboring envelopes of different host ranges (J. Virol. 65: 3887–3890).

Example 2

Preparation and Infection of the Human Osteoblast Precursors

Cells from the periosteum of a femur of a 13 year old female patient were prepared by culturing pieces of preriosteal tissue in Opti-MEM (Gibco BRL; Basel; Switzerland) supplemented with 10% FBS in 95% air/5% $CO_2$ at 37° C. for 3 weeks. At confluency cells were trypsinised and plated in a 25 $cm^2$ flask. At 70–80% confluency, cells were incubated for 3 hours at 37° C. (90% humidity) with the recombinant virus containing the SV40-T antigen, prepared as described in example 1, in the presence of 20 µg/ml DEAE dextran. After the infection, the culture medium was changed with α-MEM supplemented with 10% FBS and penicillin/streptavidin. After 3 to 4 passages non-infected primary cells stopped growing, while cells from the infected pool continued to proliferate until passage 12–15. These cells expressing the SV40 T antigen were named hPOB.

At passage 9, hPOB cells were infected, as described above, with a recombinant virus carrying the hTERT gene. These cells were called hPOBtert.

Example 3

Culture and Differentiation of hPOBtert

Infected cells were cultured in the presence of α-MEM supplemented with 10% FCS and Penicillin/Streptavidin. This medium is referred as the basal medium. For differentiation, cells were seeded on collagen I (30 µg/ml; bovine skin-type I collagen; Roche Biomedical; Basel; Switzerland) coated dishes at a density of 12000 cells/$cm^2$ in the basal medium. Confluent cells were incubated for 2 to 21 days in the basal medium supplemented with 1 mM β-glycerophosphate and 50 µg/ml ascorbate supplemented with 10 nM dexamethasone or 10 nM vitamin $D_3$ (vitD).

The mineralized matrix formation was followed in infected cells cultured at day 0 and 21 after confluency under the differentiation conditions. After cell fixation by incubation with ice cold 70% ethanol for 1 hour, the mineralized matrix was stained with the Alzarin Red-S based calorimetric reaction.

Example 4

Alkaline Phosphatase Activity Measurement hPOBtert cells cultured under the differentiation conditions were harvested at day 0, 2, 4, 6 and 9 after confluency and homogenated in a lysis buffer containing 10 mM Tris (pH 7.5), 0.5 mM MgCl2 and 0.1% 10×Triton. Alkaline phosphatase (ALP) activity was measured on cell homogenate using a commercially available kit (Sigma), the results were normalized to total protein content, as measured by the Bradford assay method.

Example 5

Immunodetection of the SV40-T Antigen Protein in hPOB Cells hPOB cells grown at 90% confluency on eight-well chambered glass slides were washed with Hanks saline buffer (HBSS) and fixed 30 min at least at −20° C. with an ice cold mixture of methanol/acetone (v/v). Fixed cells were incubated 1 hour at room temperature with a mouse monoclonal antibody directed again the SV40-T antigen (1/30 dilution) in a buffer containing 0.05 M Tris pH 8.6, 1.8% NaCl and 0.2% polyethylene glycol (TNP buffer) supplemented with 1% bovine serum albumin (BSA). After 3 washes with the TNP buffer, cells were incubated 1 hour at room temperature in the dark with TNP buffer supplemented with 1% BSA and with a fluorescin-conjugated anti-mouse IgG antibody (1/250 dilution). Cell nuclei was observed with a fluorescent microscope (Zeiss).

Example 6

RNA Preparation and Expression Analysis by RT-PCR

At day 6 after confluency, cells cultured under the differentiation conditions were washed with HBSS and stored at −80° C. until RNA extraction using the RNeasy Total RNA Purification System (Qiagen AG, Basle, Switzerland).

Reverse transcription was performed with an input of 10 µg of total RNA using the $1^{st}$ strand cDNA synthesis kit for RT-PCR (AMV; Roche Biomedical, Basle, CH) with oligo d$(T)_{15}$ as primer. Primers used for the amplification of cDNA's of interest were synthesized by Mycrosynth (Windisch, CH).

The sequence of the forward and reverse primers was, respectively:

```
                                         (SEQ ID NO: 1)
5'-GTTGCTATCCAGGCTGTG-3' and (SEQ ID NO: 2)
5'-CATAGTCCGCCTAGAAAGC-3' for the actin gene, (SEQ ID NO: 3)
5'-ATGAGAGCCCTCACACTCCT-3', and
```

-continued

5'-GATGTGGTCAGCCAACTCGT-3', for the osteocalcin gene, (SEQ ID NO: 4)

5'-AGAGGTGGTGGAAGAAACTG-3', and (SEQ ID NO: 5)

5'-GCTTCTGCTTCTCAGTCAGA-3' for the osteonectin gene, (SEQ ID NO: 6)

5'-CAGTGATTTAGGGCGCATTC-3' and (SEQ ID NO: 7)

5'-GAAATGCGCCTAGGCACATC-3' for the Cbfa-1 gene. (SEQ ID NO: 8)

The PCR reaction was heated for 2 cycles to 98° C. for 1 min, 60° C. for 2 min and 72° C. for 2 min and then cycled 28 times through a 1 min denaturation step at 94° C., a 1 min annealing step at 60° C. and a 2 min extension step at 72° C. in a DNA thermal cycler apparatus (Bioconcept, Allschwill, Switzerland). Actin primers were included in the reaction as an internal control. PCR products (10 µl) were separated on a 2% agarose gel and visualized by ethidium bromide staining. Quantification of the PCR products was performed using the densitometric NIH Imager Program.

Example 7

TRAP Assay

The telomerase repeat amplifacation protocol (TRAP) assay was performed on cell extracts as previously described (Kim et al., Science 266 (1994), 2011–2015). $10^6$ cells were lysed in 200 µl of lysis buffer (10 mM tris-HCl, pH 7.5, 1 mM $MgCl_2$, 1 mM EGTA, 0.5% CHAPS, 10% Glycerol). The cell lysate was centrifuged for 20 min at 14000 rpm at 4° C. The supernatant was collected and the protein amount was determined using the Bradford protein assay (Biorad). 2 µl of cell lysate corresponding to 50 µg protein was added to the 48 µl of reaction mix containing: 5 µl TRAP buffer 10×(200 mM tris-HCl, pH 8.3, 15 mM $MgCl_2$, 10 mM EGTA, 680 mm KCl, 0.5% Tween), 0.25 µl 10 mM dNTPs, 1.8 µl 50 ng/µl primer M2, 1.8 µl 50 ng/µl primer CX and 0.4 µl 5U/µl taq polymerase. The sequence of the primers was:

5'-AATCCGTCGAGCAGAGTT-3' for the primer M2, and (SEQ ID NO: 9)

5'-CCCTTACCCTTACCCTTACCCTAA-3' for the primer CX. (SEQ ID NO: 10)

The telomerase reaction was continued for 30 min at room temperature before the PCR reaction was started: heating for 1 cycle to 94° C. for 2 min, and then cycling 30 times through a 10 sec denaturation step at 94° C., a 25 sec annealing step at 50° C. and a 30 sec extension step at 72° C., and one additional cycle was performed with a 15 sec denaturation step at 94° C., a 25 sec annealing step at 50° C. and a 1 min extension step at 72° C. in a DNA thermal cycler apparatus. 20 µl of the PCR product was separated in a 10% acrylamide gel and visualized by SYBR green I gel staining (Molecular Probes).

Example 8

Karyotype Analysis

Semi-confluent cultures were sent to the Cell Culture Laboratory at Children's Hospital of Michigan for karyotypic analyses. For chromosome study exponentially growing cultures were treated with 0.04 µg/ml of colcemid for 1–2 hours, trypsinized and treated with 0.0375 M KCl for 9 minutes and fixed in 3:1 methanol:glacial acetic acid mixture. The suspension was centrifuged and washed a couple of times with fixative and finally dropped on cold wet slides as previously reported (Peterson, W. D. Jr. et al, Methods in Enzymology 58; 164–178, 1979). Slides were air dried and stained with 4% Giemsa solution. Giemsa stained slides were utilized for ploidy distribution, counts and constitutional aberrations. For trypsing Giemsa banding (GTG), karyotypes were prepared by modified procedure of Seabright, (Seabright, M. A, Lancet; 971–972, 1971) (2). The slides were aged at 60° C. on a slide warmer for 16–20 hours, immersed in 0.025% trypsin for 1–2 seconds, stained with 4% Giemsa solution for 11 minutes, washed in buffer, dried and mounted in permount. Well banded metaphases were karyotyped using the AKSII Image Analysis system.

A minimum of 7 karyotypes were prepared from these prints and arranged according to Standard human karyotype. The karyotypes were described according to standard nomenclature (ISCN An international System for Human Cytogenetic Nomenclature, Mitelman F. (ed.) Basle: Karger, 1995).

Two chromosome markers were investigated in more detail. The chromosomes 11 and 15 which showed prominent involvement in hPOB cells, now show established markers in hPOB-tert cells. The isoenzyme phenotype patterns are concordance with those of h-POB cells. These findings identify hPOB-tert cells with virtual certainly as a derivative of hPOB cells. Cells other than those of cell line hPOB-tert (passage 39) were not detected in the culture.

SEQUENCE LISTING

<160> NUMBER OF SEQ ID NOS: 10

<210> SEQ ID NO 1
<211> LENGTH: 18
<212> TYPE: DNA
<213> ORGANISM: artificial
<220> FEATURE:
<223> OTHER INFORMATION: primer

```
<400> SEQUENCE: 1
gttgctatcc aggctgtg                                              18

<210> SEQ ID NO 2
<211> LENGTH: 19
<212> TYPE: DNA
<213> ORGANISM: artificial
<220> FEATURE:
<223> OTHER INFORMATION: primer

<400> SEQUENCE: 2
catagtccgc ctagaaagc                                             19

<210> SEQ ID NO 3
<211> LENGTH: 20
<212> TYPE: DNA
<213> ORGANISM: artificial
<220> FEATURE:
<223> OTHER INFORMATION: primer

<400> SEQUENCE: 3
atgagagccc tcacactcct                                            20

<210> SEQ ID NO 4
<211> LENGTH: 20
<212> TYPE: DNA
<213> ORGANISM: artificial
<220> FEATURE:
<223> OTHER INFORMATION: primer

<400> SEQUENCE: 4
gatgtggtca gccaactcgt                                            20

<210> SEQ ID NO 5
<211> LENGTH: 20
<212> TYPE: DNA
<213> ORGANISM: artificial
<220> FEATURE:
<223> OTHER INFORMATION: primer

<400> SEQUENCE: 5
agaggtggtg gaagaaactg                                            20

<210> SEQ ID NO 6
<211> LENGTH: 20
<212> TYPE: DNA
<213> ORGANISM: artificial
<220> FEATURE:
<223> OTHER INFORMATION: primer

<400> SEQUENCE: 6
gcttctgctt ctcagtcaga                                            20

<210> SEQ ID NO 7
<211> LENGTH: 20
<212> TYPE: DNA
<213> ORGANISM: artificial
<220> FEATURE:
<223> OTHER INFORMATION: primer

<400> SEQUENCE: 7
cagtgattta gggcgcattc                                            20

<210> SEQ ID NO 8
```

-continued

```
<211> LENGTH: 20
<212> TYPE: DNA
<213> ORGANISM: artificial
<220> FEATURE:
<223> OTHER INFORMATION: primer

<400> SEQUENCE: 8
gaaatgcgcc taggcacatc                                               20

<210> SEQ ID NO 9
<211> LENGTH: 18
<212> TYPE: DNA
<213> ORGANISM: artificial
<220> FEATURE:
<223> OTHER INFORMATION: primer

<400> SEQUENCE: 9
aatccgtcga gcagagtt                                                 18

<210> SEQ ID NO 10
<211> LENGTH: 24
<212> TYPE: DNA
<213> ORGANISM: artificial
<220> FEATURE:
<223> OTHER INFORMATION: primer

<400> SEQUENCE: 10
cccttaccct taccottacc ctaa                                          24
```

What is claimed is:

1. An immortalized pre-osteoblast cell line obtained from a human bone periostal layer, expressing at least one oncogene for uncoupling the normal cell cycle and containing a construct that can express a telomerase gene, and which is capable of differentiating to osteoblasts, wherein the immortalized cell line is CNCM I-2573.

2. A method for detecting substances controlling the differentiation of pre-osteoblasts to osteoblasts comprising providing the immortalized pre-osteoblast cell line according to claim 1 in an assay; and screening the assay for detecting substances controlling the differentiation of pre-osteoblasts to osteoblasts.

3. A method for detecting substances enabling improved bone formation, maintenance of bone mass, bone repair and for preventing the onset of osteoporosis comprising: providing the immortalized pre-osteoblast cell line according to claim 1 in an assay; and screening the assay for detecting substances enabling improved bone formation, maintenance of bone mass, bone repair and for preventing the onset of osteoporosis.

* * * * *